(12) United States Patent
Biedermann et al.

(10) Patent No.: US 7,211,086 B2
(45) Date of Patent: May 1, 2007

(54) LOCKING DEVICE FOR SECURING A ROD-SHAPED ELEMENT IN A HOLDING ELEMENT CONNECTED TO A SHANK

(75) Inventors: Lutz Biedermann, VS-Villingen (DE); Jürgen Harms, Karlsruhe (DE)

(73) Assignee: Biedermann Motech GmbH (DE)

( * ) Notice: Subject to any disclaimer, the term of this patent is extended or adjusted under 35 U.S.C. 154(b) by 446 days.

(21) Appl. No.: 10/329,888

(22) Filed: Dec. 26, 2002

(65) Prior Publication Data

US 2003/0125741 A1    Jul. 3, 2003

(30) Foreign Application Priority Data

Dec. 28, 2001    (DE)    ................. 101 64 323

(51) Int. Cl.
*A61B 17/70* (2006.01)

(52) U.S. Cl. .................. 606/61; 606/71; 606/72

(58) Field of Classification Search .............. 606/61, 606/60, 72
See application file for complete search history.

(56) References Cited

U.S. PATENT DOCUMENTS

| | | | | |
|---|---|---|---|---|
| 2,440,944 A | * | 5/1948 | Green | ................. 411/282 |
| 5,443,467 A | * | 8/1995 | Biedermann et al. | ......... 606/65 |
| 5,672,176 A | * | 9/1997 | Biedermann et al. | ......... 606/61 |
| 5,690,630 A | * | 11/1997 | Errico et al. | .................. 606/61 |
| 5,797,911 A | | 8/1998 | Sherman et al. | ............... 606/61 |
| 5,928,233 A | * | 7/1999 | Apfelbaum et al. | .......... 606/61 |
| 6,077,262 A | * | 6/2000 | Schlapfer et al. | ............. 606/61 |
| 6,443,953 B1 | * | 9/2002 | Perra et al. | ................... 606/61 |
| 6,835,196 B2 | * | 12/2004 | Biedermann et al. | ......... 606/61 |

FOREIGN PATENT DOCUMENTS

WO     WO 98/25534     6/1998

* cited by examiner

*Primary Examiner*—Tom Barrett
*Assistant Examiner*—David A. Izquierdo
(74) *Attorney, Agent, or Firm*—Christie, Parker & Hale LLP

(57) ABSTRACT

A locking device is provided for securing a rod in a receiving part, in particular a polyaxial bone screw. The locking device has a sleeve-type element with a cylindrical outer face and is dimensioned such that the element is displaceable between the legs of the receiving part. The element has an inner thread for receiving an inner screw. An outer nut can be screwed on to an outer thread of the legs to fix the element. The element acts on a pressure element provided in the receiving part to fix the position of the head of the polyaxial bone screw and the inner screw acts on the rod to fix it. The element is preferably provided with slits. During screwing in of the inner screw, the element splays out against the outer nut and thus effectively prevents loosening or detaching.

13 Claims, 2 Drawing Sheets

LOCKING DEVICE FOR SECURING A ROD-SHAPED ELEMENT IN A HOLDING ELEMENT CONNECTED TO A SHANK

The invention relates to a locking device to be used in spinal column or accident surgery for securing a rod-shaped element in a holding element connected to a shank. The invention further relates to an element with a shank and a holding element connected to it for connecting to a rod with a locking device of this kind, in particular a polyaxial bone screw.

From WO 98/25534 a polyaxial bone screw is known, in which the head of the bone screw and the rod can be fixed relative to the receiving part independently of one another.

The object of the invention is to create a locking device of the kind initially described and an element with a shank and a holding element connected to it, which guarantees better securing against loosening or detaching of the locking elements and at the same time is compactly constructed.

This object is achieved by the locking device characterised in claim 1 or by the element characterised in patent claim 4. Further developments of the invention are cited in the subordinate claims.

Further features and advantages of the invention emerge from the description of embodiment examples using the figures.

Figure 1:
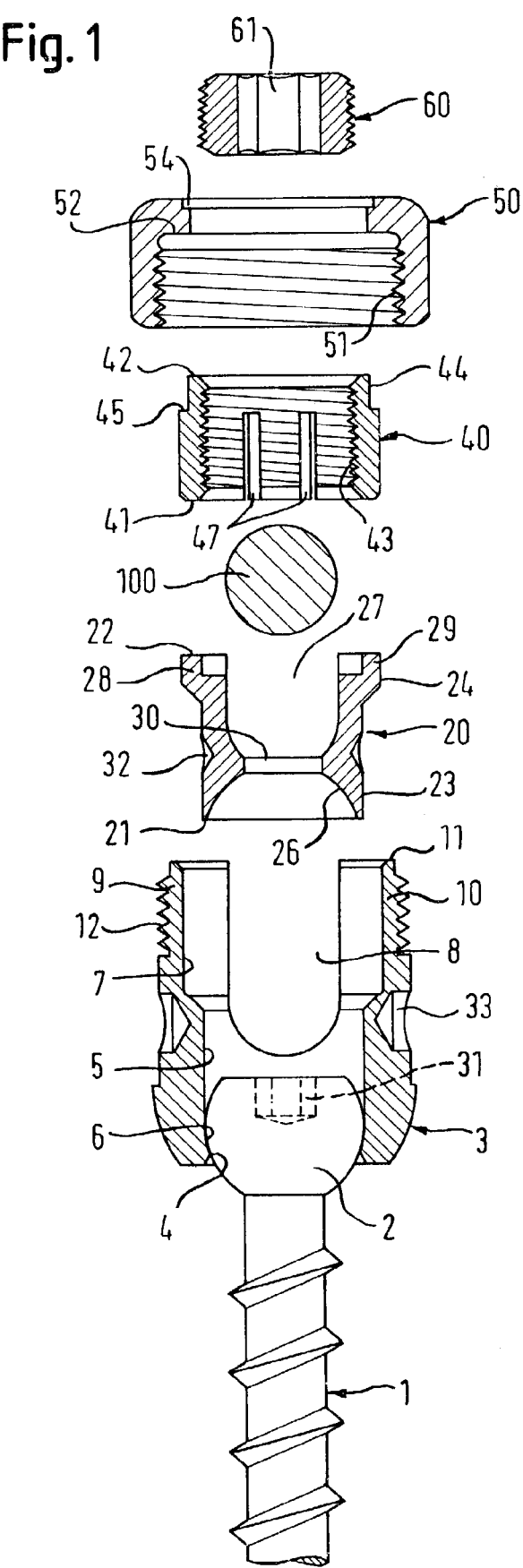
FIG. 1 shows a polyaxial bone screw according to one embodiment in exploded illustration in section.
Figure 2:
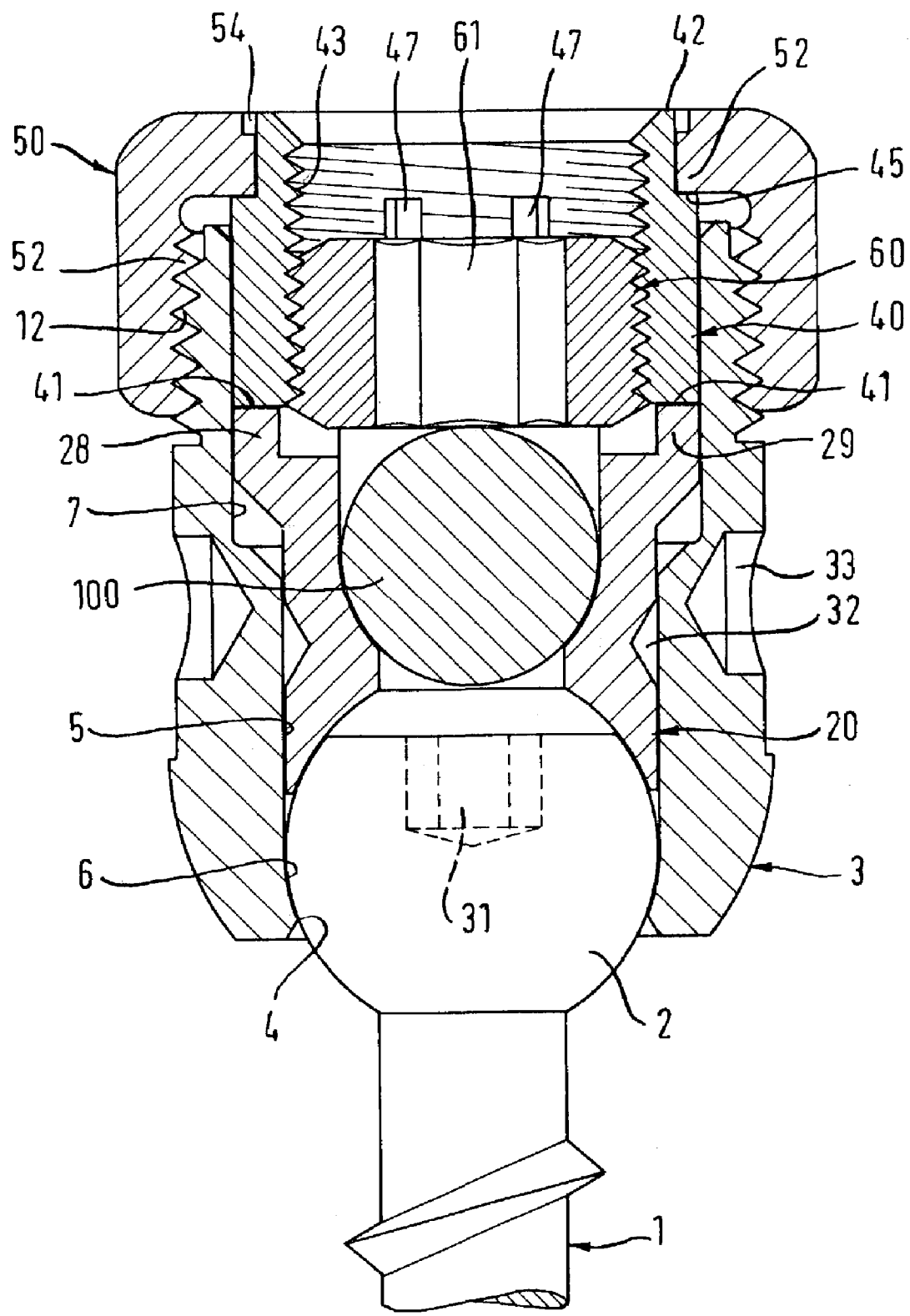
FIG. 2 shows the polyaxial bone screw of FIG. 1 in the operating state illustrated in section.

In the embodiment shown in FIGS. 1 to 2 the element according to the invention is constructed as a polyaxial screw which has a screw element with a threaded shank 1 with a bone thread and a head 2, shaped like a segment of a sphere, which is connected to a receiving part 3. The receiving part 3 has on one of its ends a first bore 4, aligned symmetrically to the axis, the diameter of which is larger than that of the thread section of the shank 1 and smaller than that of the head 2. The receiving part 3 further has a coaxial second bore 5, which is open at the end opposite the first bore 4 and the diameter of which is large enough for the screw element to be guided through the open end with its thread section through the first bore 4 and with the head 2 as far as the bottom of the second bore 5. Between the first and the second bore a small coaxial section 6 is provided, which is immediately adjacent to the first bore 4 and is constructed as spherical towards the open end, the radius being substantially identical to the section of the head 2 shaped like a segment of a sphere. The second bore 5 widens towards the end facing away from the first bore 4, forming an area 7 with a larger diameter.

The receiving part 3 further has a U-shaped recess 8, arranged symmetrically to the centre of the part, for receiving a rod 100, the bottom of which is directed towards the first bore 4 and by which two open legs 9, 10 are formed, the open end 11 of which forms the upper edge of the receiving part 3. In an area adjacent to the open end 11 the legs 9, 10 have an outer thread 12.

Further provided is a pressure element 20 with a first end 21, which in a state inserted into the receiving part 3 faces the head 2, and a second end 22 opposite the first end 21. The pressure element has adjacent to the first area 21 a first cylindrical area 23 with a diameter which is slightly smaller than that of the bore 5 adjacent to the spherical section 6, so that the pressure element can slide in the area of bore 5, in other words can be displaced towards the head 2. The first cylindrical area 23 changes with a conical outer face into a second cylindrical area 24, extending as far as the second end 22 and having a diameter which is slightly smaller than that of area 7 of the receiving part 3 to the effect that the pressure element 20 with its second cylindrical area 24 can slide in area 7 of the receiving part 3.

The pressure element further has on its first end 21 a recess 26, shaped like a segment of a sphere and widening towards the end, the spherical radius of which is chosen in such a way that in a state inserted into the receiving part it partially encompasses the head 2.

There is further on the pressure element 20, on the second end 22 opposite the recess 26 shaped liked a segment of a sphere, a U-shaped recess 27, wherein the dimensions of the U-shaped recess of the pressure element are dimensioned in such a way that in the state inserted into the receiving part 3 the U-shaped recess 8 of the receiving part and the U-shaped recess 27 of the pressure element form a channel into which the rod 100 can be placed. The depth of the U-shaped recess 27, seen in the direction of the cylindrical axis of the receiving part 3, is larger than the diameter of the rod 100 to be received, so that the pressure element 20 projects upwards above the placed in rod 100 with lateral legs 28, 29. The pressure element further has a central bore 30 extending through it, the diameter of which is dimensioned just large enough for a screwing tool to be guided through for bringing into engagement with a recess 31 provided in the head 2. In its first cylindrical section 23 further provided on the circumferential side of the pressure element are indented bores 32, which cooperate with corresponding crimped bores 33 on the receiving part 3 to hold the pressure element lightly in the position in which the channel is formed.

Further provided is a sleeve-like element 40 of cylindrical shape, with a first end 41 and a second end 42 opposite thereto, wherein the outer diameter of the element 40 is large enough for the element 40 to be able to be inserted from the open end 11 in area 7 of the receiving part 3 and to slide therein. The sleeve-shaped element 40 has a central bore with an inner thread 43 for receiving an inner screw 60. Adjacent to the second end a ring-shaped recess 44 is provided in the outer wall, by which a shoulder 45 is formed. In the embodiment according to FIG. 1 a plurality of slits 47 extends in the axial direction from the first end 41 of the element 40 through its wall as far as the level of the shoulder 45. These slits have the effect that the element 40 is mainly elastic in the horizontal direction on the one hand and in the vertical direction acts as a stable pressure ring. The axial length of the element 40 is dimensioned in such a way that the element, when it is inserted into the receiving part together with the screw head 2 and the pressure element 20 and rests with its first end 41 on the legs 28, 29 of the pressure element, projects with its shoulder 45 slightly above the edge 11 of the receiving part.

To fix the element 40 an outer nut 50, encircling the legs 9, 10 from outside, is provided, the inner thread 51 of which cooperates with the outer thread 12 of the legs 9, 10 of the receiving part 3. The outer nut 50 has at one end a projection 52, directed radially inwards, which in the screwed down state of the outer nut 50 presses on the shoulder 45 of the element 40. The axial length of the outer nut 50 is further dimensioned in such a way that in the screwed down state the outer nut just does not press on the placed in rod 100, so that it is displaceable in the channel.

The inner screw 60 can be screwed into the sleeve-type element 40. For this purpose it has a recess 61 for bringing into engagement with a screwing in tool In operation first the screw element is introduced into the receiving part 3 until the head 2 is resting against the spherical section 6. Then the pressure element 20 is inserted and held via the cooperation of the indented and crimped bores 32 in such a way that the U-shaped recess 8 of the receiving part and the U-shaped recess 27 of the pressure element 20 come to rest on top of one another. The pressure element is thus secured against falling out. In this state the surgeon screws the screw element into the bone via the recess 31. Then the rod 100 is placed in and the sleeve-type element 40 with already screwed in inner screw 60 is inserted between the legs 9, 10 from the open end 11 of the legs. The inner screw 60 is therein screwed into the element 40 only to such a distance that its side facing the rod does not yet touch the rod. The outer nut 50 is then screwed on. As long as the projection 52 of the nut directed inwards is not yet resting on the shoulder 45 of the element 40, the head 2 of the screw element is still not fixed all the time. Only with further screwing down of the outer nut 50, the projection 52 presses on the shoulder 45 and thus on the element 40, which on its part again with its first end 41 exerts a force on the legs 28, 29 of the pressure element 20, whereby it presses against the head 2 and fixes it in its position. Because the legs 28, 29 of the pressure element project above the placed in rod 100, the rod is still displaceable. The rod is then fixed by deeper screwing in of the inner screw 60 until it acts on the rod 100.

During screwing down of the outer nut a force acts on the legs 9, 10 of the receiving part, pressing them slightly inwards. The slit element 40 is thus slightly pressed together. For final firm screwing in of the inner screw 60 for fixing the rod a force component, directed radially outwards, acts via the thread flanks and widens the element 40. The element 40 thereby splays out against the legs 9, 10 of the receiving part and the thread 12 holding the outer nut, effectively preventing loosening or even detaching of the locking mechanism.

The described locking mechanism additionally guarantees that the pressure element 20 experiences forces only in the axial direction, but not in the radial direction, so its function of fixing the head is not impaired even after the inner screw has been screwed in.

In one modification the inner thread 43 of the element 40 is constructed as a left thread, while the outer thread 12 of the legs of the receiving part 3 and the thread of the outer nut are constructed as right threads.

Instead of the above-described embodiments, in which the shank 1 is constructed with a bone thread, the shank can also be constructed as a hook, as used in spinal column surgery for hooking in behind bone projections of the spinal column.

In a further modification of the polyaxial embodiments, instead of the thread shank 1 or the hook, a bar or a rod-shaped element is provided, which has a head shaped like a segment of a sphere at both ends, connected to a receiving part of the kind described. In this way an element of this kind can be used as a connecting element between two rods 100.

In a further modification the sleeve-type element 40 is rotatably connected to the outer nut. For this purpose the second end 42 of the element 40 is curved radially outwards (not illustrated in the figures), so that it engages in a ring-shaped recess 54, shown in FIGS. 1 and 2, on the upper side of the outer nut 50. In operation the outer nut with the rotatably connected element 40 is then placed as a unit on the legs and the outer nut is screwed down.

The locking device according to the invention can also be applied to a monoaxial bone screw. In this case the sleeve-type element 40 does not act on a pressure element, but acts in addition to the inner screw directly on the rod. For this purpose the element 40 is dimensioned, as far as its axial length is concerned, in such a way that when the outer nut is screwed down it presses on the rod. When the inner screw is screwed in, splaying of the element 40 takes place, as in the embodiment of the polyaxial screw, reliably preventing loosening or even detaching of the rod clamping.

What is claimed is:

1. A locking device for securing a rod-shaped element in a holding element, which comprises an open end, two open legs at the open end for receiving the rod-shaped element therebetween and an outer thread on the open legs, and which is connected to a shank, for use in spinal column or accident surgery,
   wherein the locking device comprises:
   a cylindrical element having a threadless outer wall and having an outer diameter which is dimensioned in such a way that the element can be slidably inserted between said two open legs of the holding element, a central bore with a first inner thread and at least one slit extending in the outer wall for a predetermined length and extending from the outer diameter through the interior thread of the cylindrical element;
   an inner screw having an exterior thread corresponding to the inner thread of said cylindrical element; and
   an outer nut comprising a second inner thread for cooperating with the outer thread of the open legs which, in the screwed down state, holds the cylindrical element between the open legs.

2. The locking device according to claim 1, wherein the cylindrical element has an open end and a plurality of slits extending for a predetermined length from the open end in the axial direction.

3. The locking device according to claim 1, wherein the at least one slit extends from the outer diameter to the central bore.

4. The locking device of claim 1, wherein the cylindrical element slides between the two open legs of the holding element.

5. A holding element comprising a shank and a holding portion connected to the shank for connecting to a rod,
   wherein the holding portion comprises an open end, a recess forming two legs at the open end having a U-shaped cross-section for receiving the rod, and an outer thread on the open legs;
   an outer nut having an inner thread to cooperate with the outer thread of the holding portion;
   a cylindrical element, which can be slidably inserted between the legs, having a threadless outer wall, an outer diameter, an interior thread and at least one slit extending in the cylinder wall for a predetermined length and extending from the outer diameter through the interior thread of the cylindrical element; and
   an inner screw having an external thread for cooperating with the interior thread.

6. The holding element according to claim 5, wherein the cylindrical element has an open end and a plurality of slits extending for a predetermined length from the open end in the axial direction.

7. The holding element according to one of claims 5, wherein the shank and the holding portion are polyaxially connected.

8. The holding element according to claim 7, further comprising a pressure element on which the cylindrical element acts to fix an angle of the shank.

9. The locking device of claim 8, wherein the cylindrical element contacts the pressure element.

10. The holding element according to claim 5, wherein the rod can be fixed via the inner screw.

11. The holding element of claim 5, wherein the cylindrical element slides between the two open legs of the holding element.

12. A locking device for securing a rod-shaped element in a holding element, which comprises an open end, two open legs at the open end for receiving the rod-shaped element therebetween and an outer thread on the open legs, and which is connected to a shank, for use in spinal column or accident surgery, wherein the locking device comprises:
- a cylindrical element having an outer wall and having an outer diameter which is dimensioned in such a way that the element can be inserted between said two open legs of the holding element, a central bore with a first inner thread and at least one slit extending in the outer wall for a predetermined length;
- an inner screw having an exterior thread corresponding to the inner thread of said cylindrical element; and
- an outer nut comprising a second inner thread for cooperating with the outer thread of the open legs which, in the screwed down state, holds the cylindrical element between the open legs;
- wherein the cylindrical element has two ends and, adjacent to one of its ends, a recess, forming a shoulder and wherein the outer nut has a corresponding projection which cooperates with the shoulder.

13. A holding element comprising a shank and a holding portion connected to the shank for connecting to a rod, wherein the holding portion comprises an open end, a recess forming two legs at the open end having a U-shaped cross-section for receiving the rod, and an outer thread on the open legs;
- an outer nut having an inner thread to cooperate with the outer thread of the holding portion;
- a cylindrical element, which can be inserted between the legs, having an outer wall, an outer diameter, an interior thread and at least one slit extending in the cylinder wall for a predetermined length; and
- an inner screw having an external thread for cooperating with the interior thread;
- wherein the cylindrical element has two ends and, adjacent to one of its ends, a recess, forming a shoulder and wherein the outer nut has a corresponding projection which cooperates with the shoulder.

* * * * *